United States Patent
Pauley et al.

(10) Patent No.: US 7,160,279 B2
(45) Date of Patent: Jan. 9, 2007

(54) RAPID EXPANSION TAMPON PLEDGET COMPRISING INVERTED COVERSTOCK AND PLEATS

(75) Inventors: Suzanne M. Pauley, Harrisburg, PA (US); Jeffrey M. Brown, Charlotte, NC (US); Irwin Butensky, deceased, late of Teaneck, NJ (US); by Francine Butensky, legal representative, Teaneck, NJ (US); Dane R. Jackson, New Hanover, PA (US); Van T. Pham, Dover, DE (US)

(73) Assignee: Playtex Products, Inc., Westport, CT (US)

( * ) Notice: Subject to any disclaimer, the term of this patent is extended or adjusted under 35 U.S.C. 154(b) by 63 days.

(21) Appl. No.: 10/620,397

(22) Filed: Jul. 16, 2003

(65) Prior Publication Data

US 2004/0127879 A1    Jul. 1, 2004

Related U.S. Application Data

(63) Continuation-in-part of application No. 09/677,353, filed on Oct. 2, 2000, now Pat. No. 6,595,974, which is a continuation-in-part of application No. 09/414,764, filed on Oct. 7, 1999.

(51) Int. Cl.
*A61F 13/15* (2006.01)
*A61F 13/20* (2006.01)
(52) U.S. Cl. .................................. 604/385.18; 604/904
(58) Field of Classification Search ........... 604/385.17, 604/385.18, 904, 11–15
See application file for complete search history.

(56) References Cited

U.S. PATENT DOCUMENTS

| | | | |
|---|---|---|---|
| 1,884,089 A | 10/1932 | Millner | |
| 2,330,257 A | 9/1943 | Bailey | |
| 2,391,343 A | 12/1945 | Popper | |
| 2,499,414 A | 3/1950 | Rabell | |
| 2,761,449 A | 9/1956 | Bletzinger | 128/285 |

(Continued)

FOREIGN PATENT DOCUMENTS

GB    2 227 666 A  *  8/1990

OTHER PUBLICATIONS

European Search Report, dated Jul. 22, 2004.

(Continued)

*Primary Examiner*—Michele Kidwell
(74) *Attorney, Agent, or Firm*—Ohlandt, Greeley, Ruggiero & Perle, L.L.P.

(57) ABSTRACT

A tampon pledget that expands without the aid of moisture or menses. The tampon pledget has a plurality of high resiliency, non-absorbent materials and a plurality of absorbent materials. The tampon pledget has improved comfort as compared to conventional fully compressed tampon pledgets. The tampon pledget preferably has all of its non-absorbent and absorbent materials enclosed in a coverstock. The coverstock may be inverted or turned inside out, prior to filling the coverstock with the plurality of non-absorbent and absorbent materials. The coverstock insertion end, removal end, or both are pleated to further enhance comfort during use. A removal string may be secured to the inverted and pleated coverstock, above the removal end seal, by a top loop slipknot.

45 Claims, 4 Drawing Sheets

U.S. PATENT DOCUMENTS

| | | | |
|---|---|---|---|
| 3,369,544 A | 2/1968 | Crockford | 128/285 |
| 3,706,311 A | 12/1972 | Kokx et al. | |
| 3,731,687 A | 5/1973 | Glassman | |
| 3,749,094 A | 7/1973 | Duncan | |
| 3,762,413 A | 10/1973 | Hanke | |
| 3,815,601 A | 6/1974 | Schaefer | |
| 3,834,389 A | 9/1974 | Dulle | 128/285 |
| 4,018,225 A | 4/1977 | Elmi | |
| 4,020,841 A | 5/1977 | Poncy et al. | 128/285 |
| 4,056,103 A * | 11/1977 | Kaczmarzyk et al. | 604/375 |
| 4,200,101 A | 4/1980 | Glassman | |
| 4,211,225 A | 7/1980 | Sibalis | |
| 4,212,301 A | 7/1980 | Johnson | |
| 4,266,546 A | 5/1981 | Roland et al. | |
| 4,300,561 A | 11/1981 | Kaczmarzyk et al. | 128/285 |
| 4,351,339 A * | 9/1982 | Sneider | 604/11 |
| 4,475,911 A | 10/1984 | Gellert | |
| 4,543,098 A | 9/1985 | Wolfe | |
| 4,675,217 A | 6/1987 | Forsman | |
| 4,787,895 A | 11/1988 | Stokes et al. | |
| 5,476,455 A | 12/1995 | Silber | |
| 5,542,914 A | 8/1996 | Van Iten | |
| 5,566,435 A | 10/1996 | Brown, Jr. | |
| 5,659,934 A | 8/1997 | Jessup et al. | |
| 5,755,906 A | 5/1998 | Achter et al. | |
| 5,817,077 A * | 10/1998 | Foley et al. | 604/363 |
| 5,928,184 A | 7/1999 | Etheredge et al. | 604/15 |
| 6,595,974 B1 * | 7/2003 | Pauley et al. | 604/385.18 |

OTHER PUBLICATIONS

International Search Report corresponding to PCT International Patent Application No. PCT/US2004/022111 dated Jun. 7, 2005.

* cited by examiner

RAPID EXPANSION TAMPON PLEDGET COMPRISING INVERTED COVERSTOCK AND PLEATS

RELATED APPLICATION

This application is a continuation-in-part of U.S. application Ser. No. 09/677,353 filed on Oct. 2, 2000, now U.S. Pat. No. 6,595,974, which is a continuation-in-part of U.S. application Ser. No. 09/414,764 filed on Oct. 7, 1999, pending.

BACKGROUND OF THE INVENTION

1. Field of the Invention

The present invention relates generally to an improved tampon or tampon pledget. More particularly, the present invention relates to a tampon pledget that expands rapidly when ejected from a tampon applicator, without the need for the tampon pledget contacting moisture or menses. Furthermore, the tampon pledget has a pleated coverstock, which is also inverted. Overall, the tampon pledget has improved comfort and good absorbency.

2. Description of the Prior Art

Tampon pledgets are typically compressed and set during either manufacture or placement of the pledget in a tampon applicator prior to use. In conventional tampon pledgets, the pledget's fibers will expand significantly upon initial contact with moisture, or menses once placed in a user's body. During expansion, the tampon pledget would conform to the user's body contours. Heretofore, it was thought that the tampon pledget needed to be ejected from the applicator and positioned within the user's body before expansion in order to achieve comfort.

Non-absorbent fibers have been used in a tampon pledget to provide expansion to the pledget. However, such tampon pledgets have not achieved the unexpected comfort of the tampon pledget of the present invention. Frankly, one would not think to improved comfort, and have comparable absorbency and sufficient bypass leakage protection, in a tampon pledget by combining non-absorbent and absorbent fibers. In addition, there has been a lack of appreciation that the correct ratio of non-absorbent fibers to absorbent fibers, including conventional absorbent fibers, provides improved comfort, and absorbency that is as good or better than known tampon pledgets.

In addition, the coverstock cylinder that encloses the absorbent material in a conventional tampon pledget typically does not totally enclose the absorbent material, leaving the absorbent material exposed at the ends of the tampon pledget. However, it is advantageous to totally enclose the absorbent material of the tampon pledget with the coverstock cylinder to ensure that the absorbent material remains intact. Therefore, the ends of the coverstock cylinder are gathered and bonded by means such as adhesive, heat, or ultrasonics, which result in hard seal bond areas. This hardness can be uncomfortable, especially during insertion and removal of the tampon pledget, where the hard seal bond areas may rub against the vulva-vaginal canal.

The present invention overcomes these drawbacks by providing a tampon pledget having an inverted coverstock with pleated insertion end and removal end bonds. The pleated ends of the pledget are soft and pliable thus providing a user increased comfort during insertion and removal of the tampon pledget. Also, by stringing the pledget above the pleated removal end seal, a stronger string results.

SUMMARY OF THE INVENTION

It is an object of the present invention to provide a tampon pledget that expands rapidly without the aid of moisture or menses.

It is another object of the present invention to provide such a tampon pledget that has improved comfort, and comparable or better absorbency, than known tampon pledgets.

It is still another object of the present invention to provide such a tampon pledget that has a number of non-absorbent materials and a number of absorbent materials.

It is yet another object of the present invention to provide such a tampon pledget in which the number of non-absorbent and absorbent materials are distributed together in the pledget, or blended together in a certain percent ratio.

It is a further object of the present invention to provide such a tampon pledget that has a coverstock.

It is still a further object of the present invention to provide such a coverstock that is inverted, or turned inside out.

It is yet a further object of the present invention to provide such a coverstock that is pleated on the insertion end, the removal end, or both.

It is another object of the present invention to provide a tampon pledget with a removal string secured to the inverted and pleated coverstock.

It is still another object of the present invention to provide such a tampon pledget that has the removal string secured to the inverted and pleated coverstock above the removal end seal.

It is yet another object of the present invention to provide such a tampon pledget that has the removal string secured to the inverted and pleated coverstock with a top loop slipknot.

These and other objects of the present invention will be appreciated from a tampon pledget that will expand without the aid of moisture or menses. The pledget comprises a plurality of non-absorbent materials, and a plurality of absorbent materials that are distributed or mixed with the plurality of non-absorbent materials. The tampon pledget has all of its absorbent and non-absorbent materials enclosed in a coverstock. The coverstock is inverted, or turned inside out, prior to filling the coverstock with a plurality of absorbent and non-absorbent materials. In addition, the coverstock insertion end, removal end, or both is pleated to further enhance comfort during use. A removal string may be secured to the inverted and pleated coverstock, above the removal end seal, by a top loop slipknot.

The plurality of non-absorbent materials can be made from ribbon, cut film, high resiliency fiber, or any combinations thereof. The plurality of absorbent materials can be made from powder, polymer bead, particulate, cellulosic fiber, superabsorbent, or any combinations thereof.

DETAILED DESCRIPTION OF THE INVENTION

Figure 1:
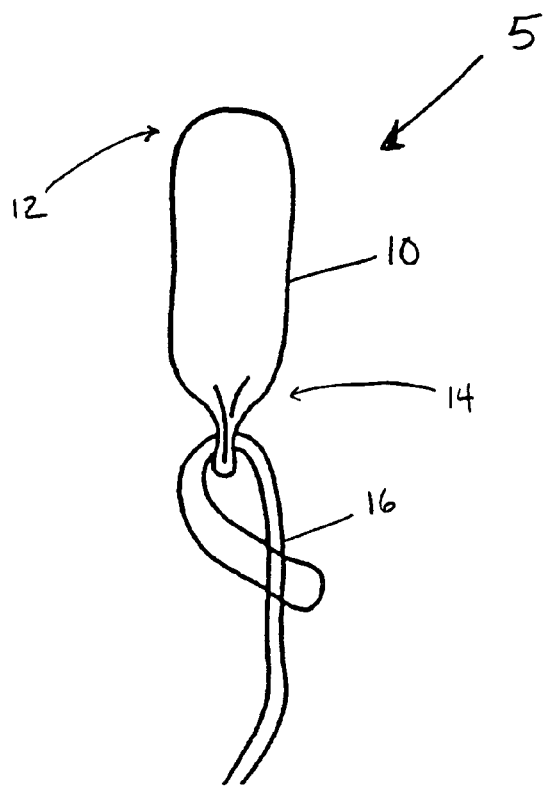
FIG. 1 is a partial plan view of a tampon pledget of the present invention.

The tampon pledget of the present invention is called a dry expansion or fast blooming tampon pledget. The expansion of the tampon pledget is immediate upon release from a tampon applicator so that the expansion occurs entirely or primarily in its dry state. Thus, moisture or menses is not needed to expand the tampon pledget.

The expansion of the tampon pledget of the present invention in its dry state occurs faster than the expansion of a conventional or known, fully compressed tampon pledget when in contact with moisture or menses. Basically, the latter requires contact with moisture or menses to cause the fibers of the tampon pledget to expand, while the former does not. Thus, the dry expansion occurs immediately upon ejection from the tampon applicator due to the nature of the non-absorbent materials and the percent ratio of non-absorbent to absorbent materials in the tampon pledget. It is preferred that the non-absorbent materials be made from non-absorbent fibers having a wet modulus, measured at 5% extension, of about 10 gram/denier to about 60 gram/denier.

With such expansion immediately upon insertion into a user's body, it has unexpectedly been found that the tampon pledget of the present invention has improved comfort.

The length of the tampon pledget of the present invention is approximately the same length as a conventional or known tampon pledget, namely about two inches. Prior to expansion, the diameter of the present tampon pledget is also approximately the same as that of conventional tampon pledgets. However, the tampon pledget of the present invention, having the same length and initial diameter of such conventional tampon pledgets, expands on its own volition when ejected from the tampon applicator and before any moisture or menses is absorbed into the tampon pledget. The expansion of the tampon pledget is to a diameter larger than that of such comparable, conventional tampon pledgets. Thus, just prior to contact with moisture or the menses of the vagina, this tampon pledget has expanded into place.

The tampon pledget of the present invention is a combination or blend of non-absorbent materials and absorbent materials. The blend may be an amorphous blend. Suitable non-absorbent materials may be made from materials, such as, for example, ribbon, cut film, high resiliency fiber, or combinations thereof. Suitable absorbent materials may be made from materials, such as, for example, one or more powders, polymer beads, particulates, cellulosic fibers, superabsorbents, or any combinations thereof.

In a preferred embodiment, the absorbent and non-absorbent materials are made from fibers that are distributed together. The distribution could be a blending or mixing. The blending could be either randomly or as desired.

The distribution could also be by layers. For example, the non-absorbent fibers can be one layer sandwiched between two layers of absorbent fibers. Alternatively, there can be two layers with one layer being non-absorbent fibers and the other layer being absorbent fibers.

In an alternative, less preferred embodiment, the non-absorbent fibers are the core of the tampon pledget. The non-absorbent fibers are basically surrounded by the absorbent fibers.

The non-absorbent fibers urge the absorbent fibers outward from the center of the tampon pledget. Thus, the non-absorbent fibers are selected to provide high wet resiliency or springiness to the absorbent structures of the tampon pledget. Thus, the non-absorbent fibers are preferably curly, crimped or springy fibers.

Such non-absorbent fibers are polyester, polypropylene, polyethylene, aramid, nylon, acrylic, bicomponent fiber, or any combinations thereof. Preferably, polyester fibers sold by Fiber Innovation Technology, Inc. under the tradename 4DG fibers are used. The 4DG fibers have a unique crenulated cross-section that results in deep grooves or channels along the longitudinal axis of the fibers. Preferably, the non-absorbent fibers are polyester, including, for example, 4DG fibers.

The non-absorbent fibers may, preferably, have a hydrophilic finish. It is preferred that the non-absorbent fibers are about 0.75 to about 30 denier fibers. More preferably, the non-absorbent fibers are a mixture of deniers. In a preferred tampon pledget, the mixture of non-absorbent fibers is a mixture with fibers that are about 6 denier and fibers that are about 19 denier. When the non-absorbent fibers are a single denier, the fibers are preferable about 15 denier.

The absorbent fibers can be any cellulosic fiber, such as, for example, rayon, lyocell, wood pulp, or cotton, or any superabsorbent, such as, for example, polyacrylate. The preferred absorbent fibers are rayon, superabsorbent or a combination of both fibers. The absorbent fibers are about 0.5 to about 30 denier. Preferably, the rayon fibers are about 1.1 to about 1.5 denier and the superabsorbent fibers are about 9 denier. Alternatively, the superabsorbent may be in powder form or granular form, rather than a fiber.

In a more preferred tampon pledget of the present invention, the tampon pledget is made of 4DG non-absorbent fibers and rayon fibers.

The ratio of non-absorbent fibers to absorbent fibers is significant. It has been found that for optimum expansion and absorbency, the percent ratio of non-absorbent fibers to absorbent fibers is about 25/75 to about 70/30. In the more preferred tampon pledget of the present invention, namely 4DG and rayon, the percent ratio of non-absorbent fibers to absorbent fibers is about 40/60.

In an alternate embodiment of the present invention, the tampon pledget is made of 4DG non-absorbent fibers, and a combination of rayon and superabsorbent absorbent fibers. The inclusion of superabsorbent fiber appears significant to improve performance over the selection of just one type of absorbent fiber.

In the alternate embodiment, the percent ratio of rayon to superabsorbent fibers is about 70/30. Thus, in the alternate embodiment of the tampon pledget of the present invention, namely 4DG, rayon and superabsorbent (such as polyacrylate), the percent ratio of non-absorbent/rayon/superabsorbent fibers is about 40/42/18.

The fiber blend of the present invention may include a surfactant. The surfactant may be anionic, cationic, non-ionic, or amphoteric. Preferably, the surfactant is nonionic. The surfactant serves primarily as a process aid. It functions to dilute and disperse any fragrance that may be added to the tampon pledget. Also, the surfactant may effect uniform absorption of menses within the tampon pledget.

The nonionic surfactant may be, for example, one or more of the following: alcohol ethoxylates, alkylphenol ethoxylates, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, or any combinations thereof. The preferred surfactant is a polyoxyethylene fatty acid ester. One such preferred surfactant is polysorbate-20. Preferably, the polysorbate-20 is that sold under the trade name Tween-20. The amount of surfactant added is between about 20 milligrams (mg) to about 140 mg per tampon pledget. Preferably, about 50 mg of surfactant is added per tampon pledget.

The tampon pledget of the present invention may also include additional additives, such as, for example, fragrance, odor absorbent, anti-bacterial agent, or any combinations thereof.

The tampon pledget of the present invention may be crimped or compressed to a certain extent for insertion into a tampon applicator. The compression should be just enough so that the tampon pledget is "spring-loaded" in the tampon applicator. By way of example, if the inside diameter of the tampon applicator is about 0.6 inches, the tampon pledget should be compressed to a diameter about 0.005 to about 0.02 inches less than the 0.6 inches, which makes the pledget about 0.595 inches to 0.58 inches in diameter. Once ejected from the tampon applicator, the tampon pledget will expand rapidly.

Immediately after ejection from the tampon applicator (and before contact with any fluid or moisture), this tampon pledget has a free diameter at its widest point from about 25% to about 300% larger than just prior to ejection. Preferably, the tampon pledget has, immediately after ejection from the tampon applicator, a free diameter at its widest point about 225% larger than just prior to ejection.

The tampon pledget of the present invention includes a coverstock that encloses, and preferably fully encloses, an amorphous blend of non-absorbent and absorbent fibers. The coverstock can be any conventional hydrophilic coverstock. However, the coverstock is preferably a non-woven, heat sealable coverstock, such as, for example, a surfactant-treated polyethylene/polypropylene bicomponent spun-bonded coverstock.

Figure 2:
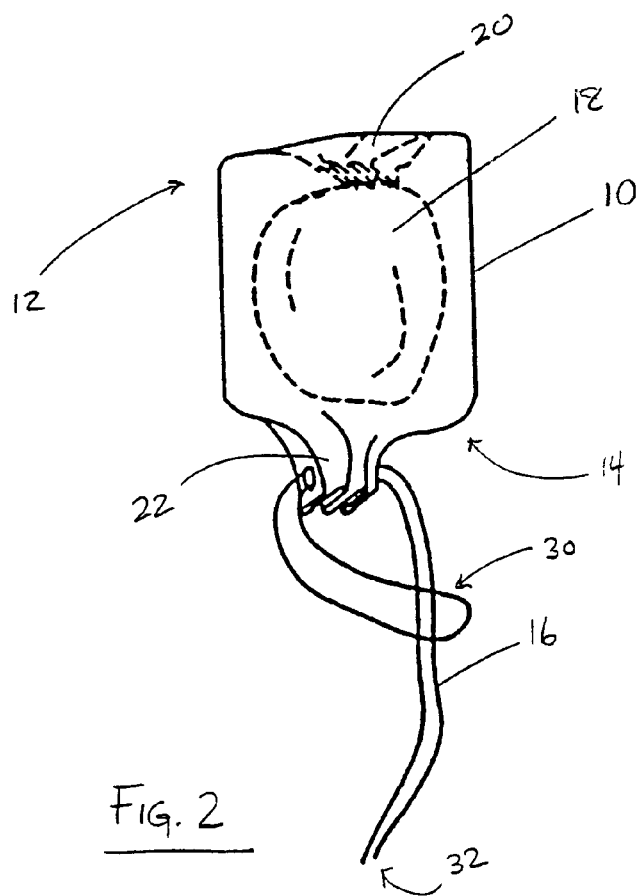
FIG. 2 is a partial plan view of the tampon pledget of FIG. 1 just prior to final forming.

Referring to FIGS. 1 and 2, a tampon pledget of the present invention is generally represented by reference numeral 5. Tampon pledget 5 has a coverstock 10, which houses fiber blend 18. Removal string 16 is secured to removal end 14 of pledget 5. It has been found that discomfort experienced during both insertion and removal of tampon pledget 5 can be minimized by inverting (turning inside out) coverstock 10.

To further enhance user comfort, it has been found that by folding or pleating either the insertion end seal 20, removal end seal 22, or preferably both, during formation of pledget 5, softer end seals 20, 22 are created. The pleated end seals 20, 22 reduce and/or eliminate discomfort when the pledget contacts the vulva-vaginal canal during use. Preferably, about 1 to about 20 pleats are formed on end seals 20, 22. More preferably, about 6 to about 10 pleats are formed.

Figure 3:
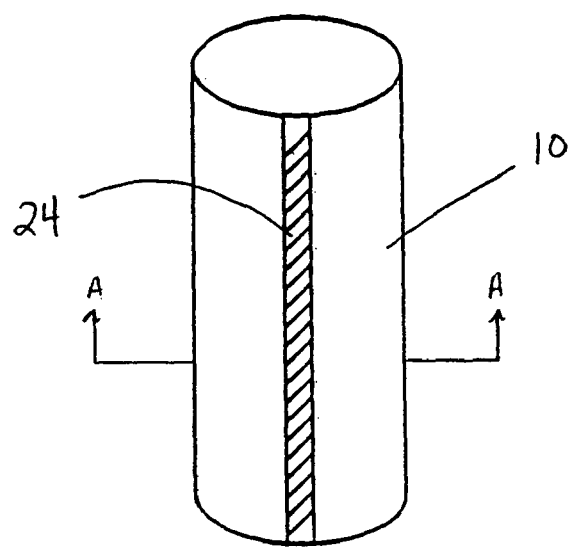
FIG. 3 is a partial plan view of the coverstock cylinder with a side seam according to the present invention.
Figure 4:
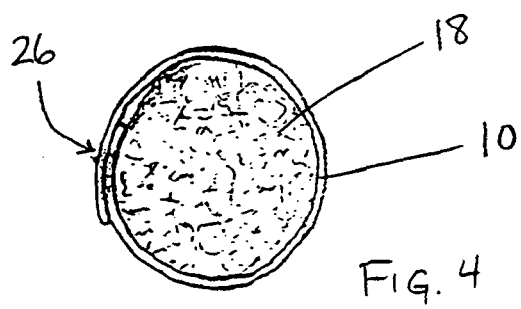
FIG. 4 is a cross-sectional view along line A—A in FIG. 3 of an alternate coverstock side seam.
Figure 5:
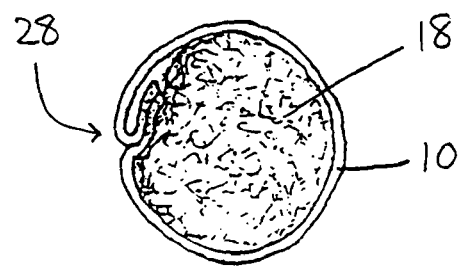
FIG. 5 is a cross-sectional view along line A—A in FIG. 3 of a preferred coverstock side seam of the present invention.

In a preferred embodiment, coverstock 10 is a flat sheet of coverstock that is rolled or formed into a cylinder with a seal along the longitudinal extant. Referring to FIGS. 3 through 5, side seam 24 of the coverstock cylinder 10 is created by rolling flat coverstock into a tube. Side seam 24 is sealed by any conventional method known to those skilled in the art, such as, for example, adhesive, heat, or ultrasonics. As shown in FIG. 4, if the side seam is an overlapped type seam 26, the inversion of the coverstock cylinder does not remove the hard seal from direct contact with the vulva-vaginal canal.

In a preferred embodiment of the present invention shown in FIG. 5, an external fin seal 28 is formed prior to inverting coverstock cylinder 10. The hard fin seal 28 is fully enclosed within coverstock cylinder 10 upon inversion of the coverstock cylinder. Thus, fin seal 28 is removed from direct contact with the vulva-vaginal canal resulting in greater comfort to the user during both insertion and removal of tampon pledget 5.

Figure 6:
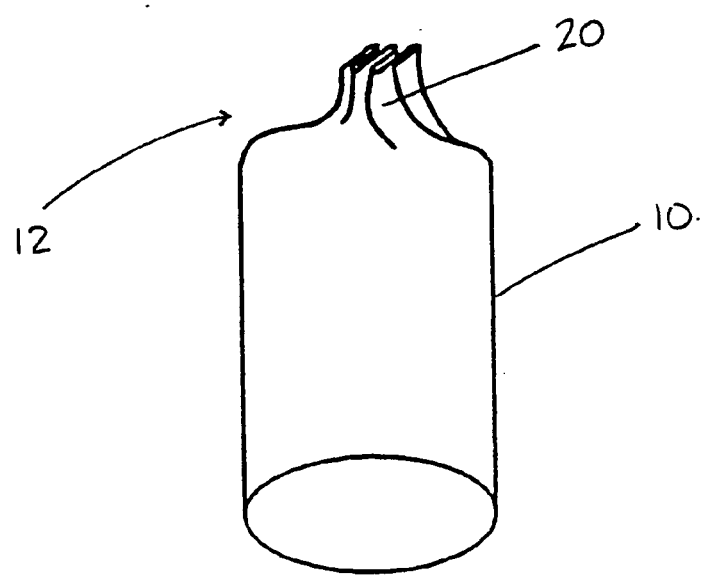
FIG. 6 is a partial plan view of a coverstock cylinder with a pleated insertion end seal according to a tampon pledget of the present invention.

Referring to FIG. 6, once coverstock cylinder 10 is formed, the coverstock at insertion end 12 is pleated. The pleated coverstock at insertion end 12 is then gathered and pleated insertion end seal bond 20 is formed.

Figure 7:
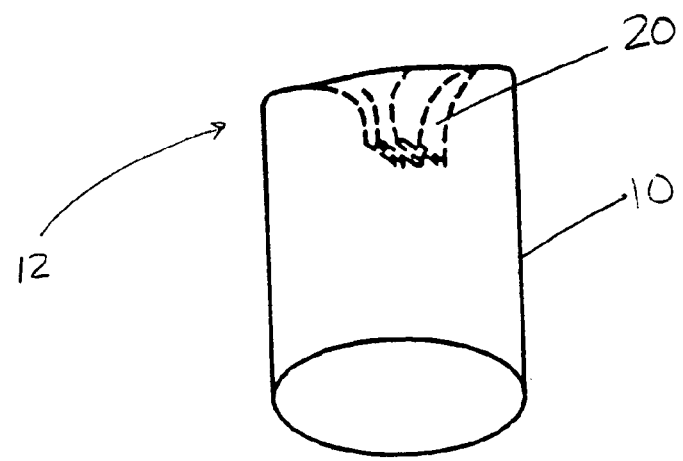
FIG. 7 is a partial plan view of the coverstock cylinder of FIG. 6 after inversion according to the present invention.

Referring to FIG. 7, prior to filling coverstock cylinder 10 with the blend of non-absorbent and absorbent fibers 18, and after the formation of the pleated insertion end seal bond 20, coverstock cylinder 10 is inverted (turned inside out). The inversion of coverstock cylinder 10 places the pleated insertion end seal bond 20 within the coverstock cylinder and removes pleated insertion end seal bond 20 away from direct contact with the vulva-vaginal canal. As a result, the user should experience greater comfort when inserting tampon pledget 5.

Figure 8:
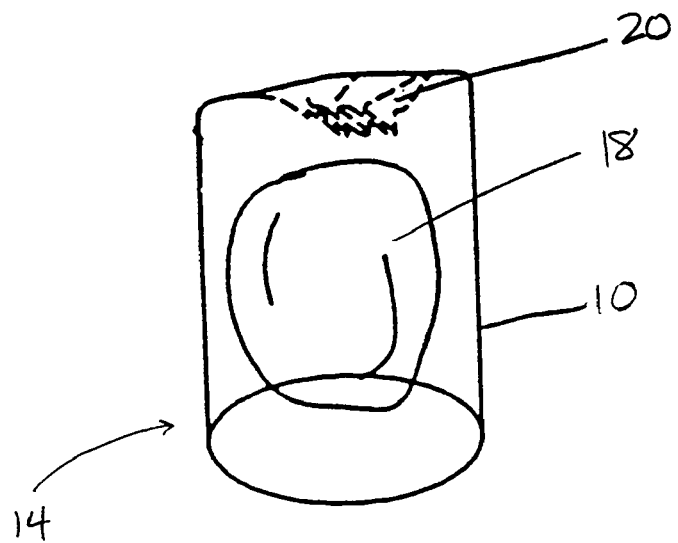
FIG. 8 is a partial plan view of the coverstock cylinder of FIG. 7 loaded with the fiber blend according to the present invention.
Figure 9:
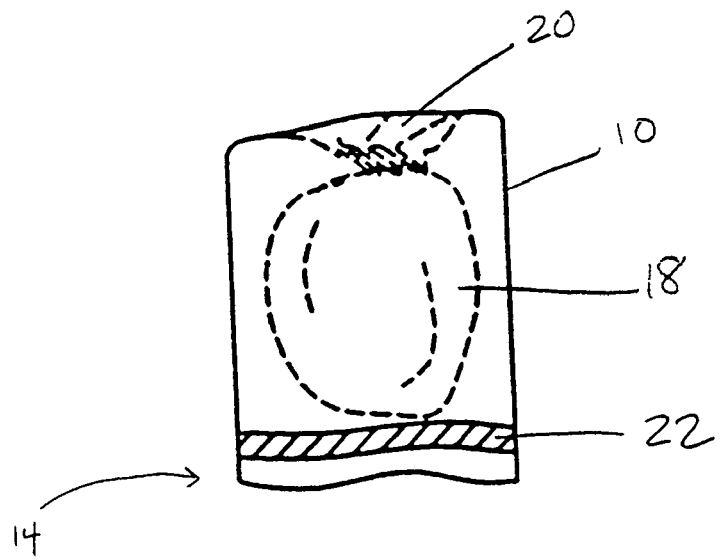
FIG. 9 is a partial plan view of the coverstock cylinder of FIG. 8 after forming a bond seal at the removal end according to the present invention.

Now referring to FIGS. 8 and 9, once coverstock 10 is inverted, it is filled with a blend of absorbent and non-absorbent fiber 18. Coverstock 10 is then sealed at the removal end 14 (i.e. the end distal of the insertion end) and a removal end seal bond 22 is formed.

Referring again to FIGS. 1 and 2, to avoid a hard removal end seal bond 22, which may result in discomfort during removal of tampon pledget 5, the removal end seal bond is pleated.

Removal string 16 is secured to removal end 14 of coverstock 10. Removal string 16 may be secured to removal end 14 by any method known in the art.

In a preferred embodiment of the present invention, removal string 16 is secured to removal end 14 at a point above removal end seal bond 22. By securing the string above removal end seal bond 22, it has been unexpectedly found that the pullout force required to break the string free from the inverted and pleated coverstock is significantly increased. As a result, string breakage during use is significantly reduced and/or eliminated.

Preferably, removal string 16 is secured to coverstock 10 using a top-loop slipknot. Removal string 16 is looped and passed through the soft inverted and pleated coverstock 10 above removal end seal bond 22. Loop 30 is pulled back around and free ends 32 of removal string 16 are passed through the loop to form a slipknot. When free ends 32 are pulled away from loop 30, loop 30 slides up pleated removal end 14 and the pleated removal end becomes further gathered and removal string 16 is further secured to tampon pledget 5.

The data set forth below in Tables 1 through 3 demonstrates the additional strength of removal string 16 as a result of stringing above the end seal bond, using the top loop stringing method described above, and pleating the removal end of coverstock 10. The samples below are made with the tampon pledget of the present invention. The string pulling speed is 5 inches per minute. For the stringing above the seal bond, the string is placed about ⅜ inches above the bottom of the pledget bag. An asterisk (*) represents a string breakage.

TABLE 1

String pull-out force for string through seal bond.
String Through Seal Bond

| 8-Pleats w/top loop- Samples | String Pull-out Force (lb.) |
|---|---|
| 1 | 4.0 |
| 2 | 7.8 |
| 3 | 5.3 |
| 4 | 3.7 |
| 5 | 8.9 |
| 6 | 5.4 |
| 7 | 4.4 |
| 8 | 4.4 |
| 9 | 4.5 |
| 10 | 4.0 |
| 11 | 8.4 |
| 12 | 4.3 |
| Ave. | 5.43 |
| STD. | 1.855 |

TABLE 2

String Pull-Out Force for String Above Seal Bond With Conventional Knot.
String Pull-Out Force (lb)

| Sample | 2 Pleats | 4 Pleats | 6 Pleats | 8 Pleats | 10 Pleats |
|---|---|---|---|---|---|
| 1 | 4.9 | 11.7 | 11.0 | 12.3 | 14.1 |
| 2 | 5.1 | 4.0 | 10.2 | 10.5 | 8.0* |
| 3 | 5.7 | 7.8 | 10.5 | 10.5 | 14.1 |
| 4 | 5.6 | 8.9 | 10.7 | 8.5 | 12.4 |
| 5 | 3.8 | 6.5 | 10.2 | 13.0 | 11.7 |
| 6 | 4.3 | 7.5 | 11.2 | 9.0 | 12.5 |
| 7 | 6.1 | 7.8 | 14.0 | 15.0 | 12.0 |
| 8 | 3.9 | 8.3 | 13.3 | 16.0* | 13.5 |
| 9 | 4.2 | 10.0 | 10.4 | 13.7 | 14.5* |
| 10 | 4.6 | 8.6 | 12.0 | 8.2 | 13.7 |
| 11 | 5.2 | 7.9 | 11.8 | 12.0 | 14.6 |
| 12 | 5.2 | 9.2 | 11.6 | 12.4 | 15.6 |
| Ave. | 4.88 | 8.18 | 11.41 | 11.76 | 13.06 |
| STD | 0.735 | 1.873 | 1.218 | 2.498 | 1.977 |

TABLE 3

String Pull-Out Force for Pledget of Present Invention
String Above Seal Bond

| Samples | 2-Pleats w/top loop | 4-Pleats w/top loop | 8-Pleats w/top loop |
|---|---|---|---|
| 1 | 15.0* | 16.0* | 13.0* |
| 2 | 16.0* | 14.0* | 14.5* |
| 3 | 15.5* | 14.5* | 17.0* |
| 4 | 14.7* | 15.2* | 15.5* |
| 5 | 16.1 | 16.6 | 16.0* |
| 6 | 11.0 | 13.5* | 14.0* |
| 7 | 13.0 | | 16.5 |
| 8 | 16.7* | | 17.5* |
| 9 | 12.0 | | 15.5* |
| 10 | 14.5* | | 15.5* |
| 11 | 14.5 | | 16.0* |
| 12 | 15.5* | | 10.0 |
| Ave. | 14.54 | 14.97 | 15.08 |
| STD. | 1.723 | 1.191 | 2.032 |

As demonstrated by the data in Table 3, pledgets with an inverted and pleated coverstock, having the string secured above the removal end seal with a top loop knot, demonstrate greater string strength, as evidenced by the higher force required to pull-out of the pledget and/or break compared to those samples in Tables 1 and 2.

Removal string 16 may be made from any material known to those skilled in the art such as, for example, cotton, rayon, polyester, or any combinations thereof. In addition, other suitable materials for the removal string include, for example, nylon, polypropylene, or any combinations thereof.

If the material is in fiber form, it may be formed into a removal string by twisting, knitting, braiding, crocheting, or weaving. Alternately, removal string 16 may be formed by spinning a monofilament string directly from the material being used. The removal string 16 may be treated with any antiwick agent, such as, for example, wax, to reduce the wicking potential of the removal string.

The cross section of removal string 16 does not have to be round. For example, a generally rectangular cross section, as in a woven ribbon, may also be acceptable.

To further avoid breakage during the removal of the tampon pledget, the cumulative strength of the removal string(s), as attached to the tampon pledget, should be equal to or greater than the anchoring strength of the removal string to the tampon pledget.

In a preferred embodiment, removal string 16 is an antiwick treated, twisted (3 to 8 strands) cotton, with a linear weight of 0.2 to 0.8 grams per yard.

By the inherent rapid, dry expansion of tampon pledget 5 of the present invention, the tampon pledget conforms during insertion more quickly to the user. Also, there is no need for moisture to contact tampon pledget 5 and be absorbed into the pledget to cause the expansion. The fact that tampon pledget 5 more quickly conforms to the user apparently results in the improved comfort.

The present tampon pledget 5 having non-absorbent fibers, and especially the percent ratio of non-absorbent to absorbent fibers, and a hydrophilic, thermal bonded, bi-component, carded coverstock, has unexpectedly been found to achieve this improved comfort without loss of absorbency. For example, in a 102 women actual use test, 47% of the women preferred the tampon pledget of the present invention for "being comfortable to wear", as compared to just 26% for the Kotex® Security® super tampon.

The tampon pledget 5 of the present invention has also been found to have absorbency about equal to or better than known tampon pledgets. A syngyna test was conducted pursuant to FDA specified test method, reference 21 CFR 801.430. The following is a table of the results of a syngyna test conducted in a laboratory. All tested tampons had a super absorbency classification.

| TAMPON TYPE | SYNGYNA ABSORBENCY (in grams) |
|---|---|
| Present pledget | 10.7 |
| Kotex ® Security ® | 11.2 |
| Playtex ® Silk Glide ® | 10.4 |
| Playtex ® Gentle Glide ® | 10.1 |
| Tampax ® | 9.7 |

Various modifications to the present invention may be made as will be apparent to those skilled in the art. Thus, it will be obvious to one of ordinary skill in the art that the foregoing description is merely illustrative of certain preferred embodiments of the present invention.

What is claimed is:

1. A tampon pledge comprising a hydrophilic inverted coverstock, said hydrophilic inverted coverstock comprising:
   an insertion end; and
   a removal end;
   wherein said insertion end and said removal end each have one or more pleats, and wherein the hydrophilic inverted coverstock is completely turned inside out.

2. The tampon pledget of claim 1, wherein said one or more pleats is about 1 to about 20 pleats.

3. The tampon pledget of claim 2, wherein said one or more pleats is about 6 to about 10 pleats.

4. The tampon pledget of claim 1, further comprising a plurality of non-absorbent materials and a plurality of absorbent materials.

5. The tampon pledget of claim 4, wherein said plurality of non-absorbent materials and said plurality of absorbent materials are blended together.

6. The tampon pledget of claim 5, wherein said plurality of non-absorbent materials and said plurality of absorbent materials are present in a percent ratio about 25/75 to 70/30.

7. The tampon pledget of claim 5, wherein said percent ratio is about 40/60.

8. The tampon pledget of claim 4, wherein said plurality of non-absorbent materials includes a plurality of non-absorbent fibers, and wherein said plurality of absorbent materials includes a plurality of absorbent fibers.

9. The tampon pledget of claim 8, wherein said plurality of absorbent fibers are about 0.5 to about 30 denier.

10. The tampon pledget of claim 8, wherein said plurality of absorbent materials are rayon fibers having about 1.1 to about 1.5 denier.

11. The tampon pledget of claim 8, wherein said plurality of non-absorbent fibers are blended with a plurality of rayon fibers and a superabsorbent at a percent ratio of about 40/42/18, respectively.

12. The tampon pledget of claim 11, wherein said superabsorbent is in the form selected from the group consisting of powder, granular, fiber, and any combinations thereof.

13. The tampon pledget of claim 4, further comprising a surfactant that is added to said plurality of non-absorbent materials and said plurality of absorbent materials.

14. The tampon pledget of claim 13, wherein said surfactant is a nonionic surfactant.

15. The tampon pledget of claim 14, wherein said nonionic surfactant is selected from the group consisting of one or more alcohol ethoxylates, alkylphenol ethoxylates, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, and any combinations thereof.

16. The tampon pledget of claim 13, wherein said surfactant is polyoxyethylene fatty acid ester.

17. The tampon pledget of claim 13, wherein said surfactant is polysorbate 20.

18. The tampon pledget of claim 13, wherein said surfactant is present in an amount about 20 mg to about 140 mg per tampon pledget.

19. The tampon pledget of claim 13, wherein said surfactant is present in an amount about 50 mg per tampon pledget.

20. The tampon pledget of claim 1, further comprising an additional component selected from the group consisting of a fragrance, an odor absorbent, and any combination thereof.

21. A dry expanding tampon pledget comprising:
   a plurality of non-absorbent fibers;
   a plurality of absorbent fibers, wherein said plurality of non-absorbent fibers and said plurality of absorbent fibers are blended together,
   wherein a percent ratio of said plurality of non-absorbent fibers to said plurality of absorbent fibers is about 25/75 to 70/30; and
   an inverted coverstock having an interior surface adjacent to the blend of absorbent and non-absorbent fibers and an exterior surface opposite the interior surface, wherein said coverstock has a pleated insertion end bond, a pleated removal end bond, and a side seam bond, and wherein said pleated removal end bond is on the interior surface of the inverted coverstock, away from the user's body.

22. The tampon pledget of claim 21, wherein said insertion end bond and said removal end bond are pleated with about 1 to about 20 pleats.

23. The tampon pledget of claim 22, wherein said Insertion end bond and said removal end bond are pleated with about 6 to about 10 pleats.

24. The tampon pledget of claim 21, wherein said percent ratio of said plurality of non-absorbent fibers to said absorbent fibers is about 40/60.

25. The tampon pledget of claim 21, wherein said side seam bond is an external fin seal bond.

26. The tampon pledget of claim 25, wherein said side seam bond is on said inner surface of said inverted coverstock away from said user's body.

27. The tampon pledget of claim 21, further comprising a surfactant that is added to said plurally of non-absorbent fibers, said plurally of absorbent fibers, or both.

28. The tampon pledget of claim 27, wherein said surfactant is one or more nonionic surfactants selected from the group consisting of alcohol ethoxylates, alkyphenol ethoxylates, carboxylic acid esters, ethoxylated anhyd rosorbital esters, glycerol esters, poly(oxyethylene-co-oxypropylene) based surfactants, polyoxyethylene fatty acid amines, polyoxyethylene fatty acid esters, and any combinations thereof.

29. The tampon pledget of claim 28, wherein said surfactant is polyoxyethylene fatty acid ester.

30. The tampon pledget of claim 29, wherein said surfactant is polysorbate 20.

31. The tampon pledget of claim 27, wherein said surfactant is present in an amount about 20 mg to about 140 mg per tampon pledget.

32. The tampon pledget of claim 27, wherein said surfactant is present in an amount about 50 mg per tampon pledget.

33. The tampon pledget of claim 21, further comprising an additional component selected from the group consisting of a fragrance, an odor absorbent, an anti-bacterial agent, and any combinations thereof.

34. A tampon pledget comprising a hydrophilic inverted coverstock and a removal string comprising:
   an insertion end; and
   a removal end,
   wherein said insertion end and said removal end each have one or more pleats, and wherein the hydrophilic inverted coverstock is completely turned inside out, and wherein said removal string has a top loop slip knot, which secures the string to the pledget.

35. The tampon pledget of claim 34, further comprising an inverted coverstock having an insertion end and a removal end, wherein said removal end has a seal.

36. The tampon pledget of claim 35, wherein said removal string is secured to said removal end of said inverted coverstock at a position above said seal.

37. The tampon pledget of claim 35, wherein at least one of said insertion end and said removal end has one or more pleats.

38. The tampon pledget of claim 37, wherein said one or more pleats is about 1 to about 20 pleats.

39. The tampon pledget of claim 38, wherein said one or more pleats is about 6 to about 10 pleats.

40. A method of making a tampon pledget having a coverstock, said coverstock comprising an insertion end and a removal end opposite said insertion end, the method comprising the steps of:

sealing said insertion end of said coverstock, thereby forming an insertion end seal bond;
pleating said sealed insertion end;
inverting said coverstock;
filling said inverted coverstock with a plurality of non-absorbent fiber and a plurality of absorbent fiber;
sealing said removal end of said coverstock, thereby forming a removal end seal bond; and
pleating said removal end.

41. The method of claim 40, further comprising the steps of:

securing a removal string to said pleated removal end of said coverstock; and
compressing said tampon pledget to a diameter less than that of a tampon applicator to be used to house said tampon pledget.

42. The method of claim 41, wherein said removal string is secured to said coverstock at a point above said removal end seal bond.

43. The method of claim 41, wherein said removal string is secured to said coverstock by a top loop slipknot.

44. The method of claim 40, wherein said insertion end bond and said removal end bond each are pleated with about 1 to about 20 pleats.

45. The tampon pledget of claim 44, wherein said insertion end bond and said removal end bond each are pleated with about 6 to about 10 pleats.

* * * * *